United States Patent
Littell et al.

(10) Patent No.: US 11,090,254 B2
(45) Date of Patent: Aug. 17, 2021

(54) APPLICATION OF DHA TO WET SKIN FOR SELF-TANNING

(71) Applicant: Kao USA Inc., Cincinnati, OH (US)

(72) Inventors: Susan Littell, Loveland, OH (US); Emily Meiser, Cincinnati, OH (US); Wael Boutros, Mason, OH (US)

(73) Assignee: Kao USA Inc., Cincinnati, OH (US)

( * ) Notice: Subject to any disclaimer, the term of this patent is extended or adjusted under 35 U.S.C. 154(b) by 0 days.

(21) Appl. No.: 15/246,703

(22) Filed: Aug. 25, 2016

(65) Prior Publication Data

US 2018/0055760 A1    Mar. 1, 2018

(51) Int. Cl.
| | |
|---|---|
| *A61K 8/891* | (2006.01) |
| *A61K 8/86* | (2006.01) |
| *A61Q 19/04* | (2006.01) |
| *A61K 8/35* | (2006.01) |
| *A61K 8/892* | (2006.01) |
| *A61K 8/60* | (2006.01) |

(52) U.S. Cl.
CPC ............... *A61K 8/891* (2013.01); *A61K 8/35* (2013.01); *A61K 8/60* (2013.01); *A61K 8/86* (2013.01); *A61K 8/892* (2013.01); *A61Q 19/04* (2013.01)

(58) Field of Classification Search
CPC . A61K 8/891; A61K 8/86; A61K 8/35; A61K 8/892; A61K 8/60; A61Q 19/04
See application file for complete search history.

(56) References Cited

U.S. PATENT DOCUMENTS

| | | | |
|---|---|---|---|
| 5,221,534 A | 6/1993 | DesLauriers et al. | |
| 2001/0047039 A1* | 11/2001 | McManus | A61K 8/0295 516/98 |
| 2004/0013617 A1* | 1/2004 | Rick | A61Q 19/04 424/59 |
| 2005/0089484 A1* | 4/2005 | McCook | A61Q 19/04 424/59 |
| 2006/0193789 A1* | 8/2006 | Tamarkin | A61K 8/046 424/47 |
| 2009/0041690 A1* | 2/2009 | Wilmott | A61K 8/60 424/59 |
| 2009/0196894 A1* | 8/2009 | Ehlis | B82Y 5/00 424/401 |
| 2010/0273736 A1* | 10/2010 | Marchitto | A61K 8/73 514/54 |
| 2014/0296182 A1* | 10/2014 | Levin | A01N 37/02 514/63 |
| 2015/0037393 A1* | 2/2015 | Millman | A61K 8/0208 424/448 |

OTHER PUBLICATIONS

Versagel Complete (Year: 2020).*
Ivana Pantelic and Bojana Cuckovic, Alkyl Polyglucosides: An Emerging Class of Sugar Surfactants in Alkyl Polyglucosides From Natural-Origin Surfactants To Prospective Delivery Systems, 1-19 available at https://www.sciencedirect.com/science/article/pii/B9781907568657500019 (Year: 2014).*
Bobin, M.F., et al., "Effects of color adjuvants on the tanning effect of dihydroxyacetone," J. Soc. Cosmet. Chem. 35:265-272, Aug. 1984, 8 pgs.

* cited by examiner

*Primary Examiner* — Sean M Basquill
(74) *Attorney, Agent, or Firm* — Frost Brown Todd LLC

(57) ABSTRACT

A self-tanning composition for application to wetted skin after showering, and the like, which provides moisturizing and skin coloration, all over body spreadability, and easy application. The self-tanning composition comprises: a quaternary ammonium salt; a reducing sugar; and at least one silicone.

11 Claims, No Drawings

APPLICATION OF DHA TO WET SKIN FOR SELF-TANNING

FIELD OF THE INVENTION

The present invention is directed to a composition and method for imparting moisturization with the additional benefit of a self-tan to skin. More particularly, the invention is directed to a composition and method that employs a cationic charged oil-in-water (O/W) moisturizing emulsion with self-tanning ingredient(s) for application to wetted skin.

BACKGROUND

There is a great health concern with natural tanning with sunlight. Ultraviolet radiation (UVA and UVB radiation) from the sun is considered to be a leading factor in causing skin cancer. Even if not lethal, ultraviolet radiation has been acknowledged as accelerating aging and wrinkling processes on the skin. Self-tanning agents are a solution for those who want the appearance of a tan but without sun exposure.

Self-tanning agents may be formulated into a product which not only imparts a skin coloration equivalent to that from basking in the sun through the use of a chemical agent, but a vehicle that is substantive and moisturizes the skin giving the skin a healthy glow. Conventionally, these moisturizing compositions with self-tanning agents have been applied to dry skin.

Most prominent among the self-tanning agents is dihydroxyacetone ("DHA" which is also chemically known as 1,3-dihydroxy-2-propanone). DHA, after application, is believed to react with the amine groups of amino acids, peptides and proteins naturally occurring in the hydrolipid pellicle and first layers of the stratum corneum of the skin. These Maillard reactions are thought to lead to formation of brown pigments in the skin, thereby giving it an appearance similar to that of a naturally obtained tan. (see, e.g., Bobin et al., J. Soc. Cosmet. Chem. 35: 255 (1984))

Qualitative evaluation of consumer behavior has shown that the application process for products intended to deliver a self-tan can be lengthy and overly complicated. Typically, consumers feel the need to avoid water once their self-tanning agent has been applied due to the tendency for water droplets or splashes to cause streaks in the tanning color. This is partially due to the need to meticulously spread the product evenly upon the skin for even color distribution. Some women overcome this problem by pre-moisturizing their skin with another lotion before applying their self-tanning agent. Using water left on the skin after bathing or showering would help eliminate this step of applying a lotion and the use of a separate product. The present technology deposits sufficient hydrophobic materials which provide a protective element to the self-tanning composition which prevents water or towel created streaks in the color that develops. The term "streak" means a non-even deposition of the self-tanning composition on the skin where the tan coloration tends to migrate along an outer perimeter causing darker and lighter areas dissimilar to the natural color variation of the skin as a result of the formula being inadequately rubbed around upon the skin.

Reducing sugars, such as dihydroxyacetone, which react with surface amino acids via the Maillard reaction are commonly used for producing browning on the skin similar in appearance to a sun tan. It is well documented that the Maillard reaction requires a certain level of moisture in the environment to produce this browning. The present invention seeks to use the water from wetted skin to improve the color, tone, and evenness of self-tanning coloration.

BRIEF SUMMARY

The present technology provides an improved self-tanning composition comprising at least one sunless-tanner in the form of a reducing sugar, in an emulsion containing PEG-2 dimeadowfoamamidoethylmonium methosulfate, and a silicone to produce an even tanned appearance, with reduced malodor, when the self-tanning composition is applied to wet skin. The at least one self-tanner is selected from dihydroxyacetone and erythrulose. In another embodiment, the self-tanner is dihydroxyacetone.

DETAILED DESCRIPTION

The present technology provides self-tanning compositions for application to wetted skin after showering or the like, having high moisturizing effects, all over body spreadability and increased adhesion to produce a non-streaked tanned finish, and easy application with a non-greasy and non-sticky feeling.

The self-tanning composition of the present invention is an oil-in-water emulsion that spreads well when applied directly to wetted skin, and provides long lasting moisturizing effects after application. In addition, the self-tanning composition can show the above-described excellent effects simply by applying to wetted skin and then towel drying; hence, they can provide these effects only by a simple process after bathing. In addition, the formula does not leave a greasy residue.

The self-tanning composition is used by applying to wetted skin after bathing, showering, and the like. Not being bound by theory, it is thought that when applied to wetted skin, the self-tanning composition will spread evenly on the skin, and release the oil-in-water emulsions, which remain on the skin surface. As water evaporates an elegant even film composed of copolymer, hydrocarbons, glycerin, other oils, emollients and other skin benefiting materials. These ingredients synergistically provide high moisturizing effects and a smooth feeling which is substantive to skin.

The self-tanning composition is a cationic oil-in-water emulsion which comprises a combination of: (1) a reducing sugar such as dihydroxyacetone; (2) a quaternium salt (quaternary ammonium cation); and (3) at least one silicone, which together produces a suitable tanned appearance with reduced self-tanning malodor when applied to wet skin.

The quaternium salt has the following general formula:

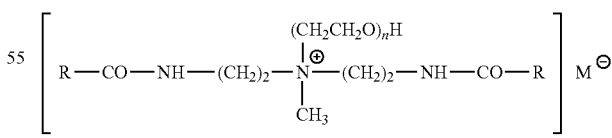

The quaternium salt may be derived from meadowfoam oil, meadowfoam acid, or meadowfoam methyl ester and may also be PEG-2 dimeadowfoamamidoethylmoniummethosulfate. The quaternium salt is present in the self-tanning composition from about 0.1% to about 5% and also from about 0.25% to about 2%. Generally, the ratio of quaternium salt to the DHA reducing sugar is from about 1:10 to about 5:1.

At least one silicone, is selected from dimethicone, dimethiconol, and mixtures thereof, and is present in the composition from about 0.1% to about 3%, by weight.

The composition may further comprise at least one block copolymer chosen from diblock copolymers, triblock copolymers, multiblock copolymers, and radial block copolymers, wherein said at least one block copolymer comprises at least one segment derived from at least one thermoplastic entity chosen from thermoplastic monomers and thermoplastic comonomers. Accordingly, the composition may contain ethylene/propylene/styrene copolymer and butylene/ethylene/styrene copolymer.

Content of the block copolymer in the self-tanning composition is from about 0.1% to about 1.5% by weight, and also from about 0.3% to about 0.7% by weight, to provide stability, ease of application, and moisturizing effects to the oil-in water emulsions.

Within the context of the self-tanning composition is a gelled oil containing block polymers. This oil may be a mineral oil as in a "Mineral Oil and Ethylene/Propylene/Styrene Copolymer and Butylene/Ethylene/Styrene Copolymer." Composition. Other representative gelled oil/block polymer compositions which may also be used include Versagel® M200 and Versagel® M750 (Penreco).

The block copolymers which can be used according to the present invention include, for example, those disclosed in U.S. Pat. No. 5,221,534 DesLauriers et al., issued Jun. 22, 1993, the disclosure of which is incorporated herein by reference. In general, the materials of the present invention contain about 80% to about 99% of an oil, and about 1% to about 20% of copolymer which includes at least one or either a di-block or tri-block polymer which consist of a hard segment, such as butadiene. Tri-block copolymers of styrene/ethylene/propylene or di-block copolymers of styrene/ethylene/propylene and styrene/butylene/ethylene are employed to gel the oil.

The invention also may include a branched fatty acid ester, in addition to the block copolymer gelled mineral oil.

Examples of the branched fatty acid ester include ethylhexyl isononanoate, isotridecyl isononanoate, octyldodecyl myristate, octyldodecyl oleate, cetyl 2-ethylhexanoate, isocetyl 2-ethylhexanoate, and isostearyl isostearate; oxyacid esters of a higher alcohol such as diisostearyl malate and cetyl lactate; and fatty acid esters of a polyol such as propylene glycol diisostearate, glyceryl tricaprylate, glyceryl tri-2-ethylhexanoate, glyceryl triisostearate, glyceryl (tricaprylate.cndot.caprate), propylene glycol dicaprylate, propylene glycol diisostearate, neopentyl glycol dicaprate, and neopentyl glycol 2-ethylhexanoate; and combinations of those materials.

The content of these branched fatty acid ester in the self-tanning composition is from about 3% to about 10%, also from about 4% to about 9%, and may also be from about 5% to about 8%.

The self-tanning composition may contain from about 5% to about 50% by weight of glycerin to provide a soft and smooth feeling on skin after application to wetted skin and excellent lasting moisturizing effects. The content of glycerin may also be from about 10% to about 45% by weight, and also from about 20% to about 35% by weight. Since a large amount of glycerin is contained therein, the self-tanning composition provides moisturizing effects when applied to skin.

Since the self-tanning composition is used by directly applying to wetted skin, they may contain the oily ingredients and glycerin in a total amount of about 40% or less, and also from about 30% to about 40% by weight, to provide wet spreadability and non-stickiness at the time of application to wetted skin, as well as a moist feeling and non-stickiness after towel drying.

The self-tanning composition contains water in an amount of from about 50% to about 80% by weight, from about 50% to about 70% by weight, and also from about 50% to about 60% by weight, from a viewpoint of stability.

The self-tanning composition may also contain from about 3% to about 20% by weight hydrocarbon oil that forms the basis for the oil-in-water emulsion. The hydrocarbon oil content may also be from about 5% to about 15% by weight and also from about 10% to about 15% by weight.

Non-limiting examples of suitable non-polar hydrocarbon oils include mineral oils and branched chain hydrocarbons (such as commercially available, for example, under the trade names Permethyl™ (Permethyl Corporation™) and Isopar™ (Exxon™)).

The self-tanning cationic moisturizing composition also includes a nonionic emulsifier or surfactant. Non-limiting examples of a nonionic emulsifier would be ceteareth-20, an alkoxylated alcohol or glyceryl monostearate.

The amount of fatty acid ester and the amount of hydrocarbon present in the oil phase to effectively moisturize and spread the ingredients on wetted skin may have a mass ratio of the fatty acid ester and the hydrocarbon oil to glycerin is also from about 1:10 to about 5:1, from about 1:5 to about 5:1, and also from about 1:5 to about 2:1.

In addition to the above-described ingredients, the self-tanning composition may contain various medicinal components, anti-inflammatory agents, UV blocking agents, botanical extracts, skin conditioning agents, skin enhancing agents, antimicrobial agents, preservatives, antioxidants, pigments, perfumes, fragrances and the like. Insofar as the effects of the invention are not impaired, the self-tanning composition may further contain a small amount of surfactants, in an amount of about 1% or less by weight and more also about 0.5% or less by weight.

Non-limiting examples of additional skin enhancing agents include *Theobromo Cacao* Extract; *Camellia Sinensis* Leaf Extract; *Fragaria Vesca* (Strawberry) Fruit Extract; *Zingiber Officinale* Leaf Extract; *Prunus Domestica* Fruit; *Punic Granatum* Leaf Extract; *Helianthus Annuus* (Sunflower) Seed Extract; *Citrus Medica Limonum* (Lemon) Peel Extract; *Chamomilla Recutita* (*Matricaria*) Flower Extract; *Helianthus Annuus* (Sunflower) Seed Oil; *Triticum Vulgare* (Wheat) Germ Oil; *Tritium Vulgare* (Wheat) Germ Extract; *Citrus Medica Limonum* (Lemon) Peel Extract; Coconut Oil; *Helianthus Annuus* (Sunflower) Seed Oil; Argan Oil; *Gardenia Tahitensis* Extract; and combinations thereof.

The composition optionally may further include ingredients that help maintain the integrity of the emulsion, such as antioxidants, chelating agents, and preservatives. Materials suitable for use in self-tanning compositions are well known to those skilled in the art. Illustrative examples of preservatives include, chlorhexidine, ethylparaben, propylparaben methylparaben, EDTA or salts thereof (such as disodium EDTA), phenoxyethanol, DMDM hydantoin, and the like, or combinations thereof. The preservative may be present in any effective amount, such as an amount of from about 0.01% to about 3% by weight of the composition.

Since the self-tanning composition is in an oil-in-water emulsion wherein oily ingredients are dispersed in an aqueous phase containing a water-soluble polymer, these emulsions can be stably blended with a large amount of glycerin, and can also provide the effects of the invention, as described above. In order to produce such stable emulsions, the oily phase/aqueous phase mass ratio is from about 10/90 to about 50/50 and also may be from about 15/85 to about 40/60.

The self-tanning composition may have a viscosity of from about 1,000 to about 100,000 mPas, also from about 5,000 to about 50,000 mPas, and also from about 5,000 to about 20,000, to achieve stability of the oil-in-water emulsions. The measurement conditions are as follows; equipment used: an RV viscometer spindle 5 @ 20 RPM; measurement temperature: 25° C.

EXAMPLES

The following examples illustrate specific aspects of the present technology and are not intended to limit the scope thereof in any respect and should not be so construed.

Example 1 (% by Mass)

| DESCRIPTION | % by Mass |
| --- | --- |
| Mineral Oil | 6.7 |
| Ethylene/Propylene/Styrene Copolymer (and) Butylene/Ethylene/Styrene Copolymer | 0.8 |
| Dihydroxyacetone | 3.5 |
| Dimethicone (and) Dimethiconol | 1.7 |
| Polyquaternium-37 | 0.76 |
| PEG-2 Dimeadowfoamamidoethylmonium Methosulfate | 0.5 |
| Erythrulose Deionized water to 100% | 0.01 |

Example 2 (% by Mass)

| DESCRIPTION | % by Mass |
| --- | --- |
| Deionized Water | To 100 |
| Glycerin | 10.0 |
| Dipropylene glycol | 3 |
| Preservative | 0.45 |
| PEG-2 Dimeadowfoam-Amidoethylmonium Methosulfate | 3.0 |
| Polyquaternium-37 | 0.5 |
| Mineral Oil (and) Ethylene/Propylene/Styrene Copolymer (and) Butylene/Ethylene/Styrene Copolymer | 10 |
| Isopropyl Palmitate | 2 |
| Shea Butter | 5 |
| Dimethicone and Dimethiconol | 2 |
| Dihydroxyacetone | 3.5 |
| Erythrulose | 0.5 |
| Fragrance | 0.5 |

Example 3

| DESCRIPTION | % by mass | % by mass | % by mass |
| --- | --- | --- | --- |
| Deionized Water | To 100 | To 100 | To 100 |
| Glycerin | 10.00 | 20.00 | 10.00 |
| Dipropylene glycol | 7.00 | 5.00 | 5.00 |
| PEG-2 Dimeadowfoam-Amidoethylmonium Methosulfate | 3.0 | 0.50 | 5.00 |
| Polyquaternium-37 | 0.75 | 0.75 | 0.75 |
| Ceteareth-20 | 0.75 | 0.25 | 0.25 |
| Mineral Oil (and) Ethylene/Propylene/Styrene Copolymer (and) Butylene/Ethylene/Styrene Copolymer | 2.5 | 7.50 | 10.0 |
| Isopropyl Palmitate | 2.00 | 2.00 | 2.00 |
| Ethylhexyl Isononanoate | 4.50 | 4.50 | 4.50 |
| Dimethicone and Dimethiconol | 3.50 | 1.75 | 1.70 |
| Dihydroxyacetone | 3.50 | 1.70 | 3.50 |
| Erythrulose | 0.01 | 0.10 | 0.50 |
| Fragrance | 0.90 | 0.60 | 0.30 |
| Preservative | 0.45 | 0.75 | 1.00 |

Procedure

1) Add water, glycerin and preservatives to a vessel large enough to hold entire batch size. Begin agitation. Mix for ~20 minutes until uniform clear gel appears. Begin to heat to 75° C.

2) In separate vessel add ingredients to Phase B and heat to same temperature as Phase A. mix until uniform. When both have reached 75° C., add Phase B to Phase A. Mix for 20 minutes, begin cooling to below 40° C.

3) Premix ingredients for part C until completely dissolved and uniform.

4) Premix ingredients for part D. slowly add Part D to part C. Mix until gelled and uniform. Once batch has reached below 40 C add ingredients susceptible to high heat and mix for 15 minutes.

What is claimed:

1. A self-tanning composition for application to wetted skin comprising:
   a) a surfactant consisting essentially of PEG-2-dimeadowfoamamidoethylmonium-methosulfate, present in the composition is from about 0.25% to about 2%, by weight;
   b) dihydroxyacetone, where the dihydroxyacetone is present from about 1% to about 5%, by weight; and
   c) at least one silicone, wherein the silicone is selected from dimethicone, dimethiconol, and mixtures thereof, and is present in the composition from about 0.1% to about 3%, by weight;
   wherein the ratio of said PEG-2-dimeadowfoam-amidoethylmonium-methosulfate to dihydroxyacetone is from about 1:10 to about 5:1.

2. A method of imparting color to the skin by applying to wetted skin a composition according to claim 1.

3. The method of claim 2 wherein the composition is a leave-on product.

4. A self-tanning composition for application to wet skin comprising:
   a. a surfactant consisting essentially of PEG-2-dimeadowfoamamidoethylmonium-methosulfate, present in the composition from 0.5% to 5%, by weight;
   b. dihydroxyacetone, where the dihydroxyacetone is present from 1% to 4%, by weight;
   c. a mixture of dimethicone and dimethiconol, present in the composition from 1% to 4%, by weight;
   d. 0.5-0.76% polyquarternium-37; and
   e. deionized water to 100%, by weight;
   wherein the ratio of the PEG-2-dimeadowfoam-amidoethylmonium-methosulfate to dihydroxyacetone is from about from about 1:5 to about 2:1.

5. The self-tanning composition of claim 4, further comprising, by weight: about 10% glycerin; about 7% dipropylene glycol; about 3% PEG-2-dimeadowfoamamidoethylmonium-methosulfate; about 0.75% Polyquaternium-37; about 0.75% Ceteareth-20; about 2.5% of a mixture of Mineral Oil (and) Ethylene/Propylene/Styrene Copolymer (and) Butylene/Ethylene/Styrene Copolymer; about 2% Isopropyl Palmitate; about 4.5% Ethylhexyl Isononanoate; about 3.5% of a mixture of Dimethicone and Dimethiconol; about 3.5% Dihydroxyacetone; about 0.1% Erythrulose; fragrance and preservative to 100%.

6. The self-tanning composition of claim 4, further comprising, by weight: about 20% glycerin; about 5% dipropylene glycol; about 0.5% PEG-2 Dimeadowfoam-Amidoethylmonium Methosulfate; about 0.75% Polyquaternium-37; about 0.25% Ceteareth-20; about 7.5% of a mixture of Mineral Oil (and) Ethylene/Propylene/Styrene Copolymer (and) Butylene/Ethylene/Styrene Copolymer; about 2% Isopropyl Palmitate; about 4.5% Ethylhexyl Isononanoate; about 1.75% of a mixture of Dimethicone and Dimethiconol; about 1.7% Dihydroxyacetone; about 0.1% Erythrulose; fragrance and preservative to 100%.

7. The self-tanning composition of claim 4, further comprising of, by weight: about 10% glycerin; about 5% dipropylene glycol; about 5% PEG-2 Dimeadowfoam-Amidoethylmonium Methosulfate; about 0.75% Polyquaternium-37; about 0.25% Ceteareth-20; about 10% of a mixture of Mineral Oil (and) Ethylene/Propylene/Styrene Copolymer (and) Butylene/Ethylene/Styrene Copolymer; about 2% Isopropyl Palmitate; about 4.5% Ethylhexyl Isononanoate; about 1.7% of a mixture of Dimethicone and Dimethiconol; about 3.5% Dihydroxyacetone; about 0.5% Erythrulose; about 0.3% fragrance and about 1% preservative.

8. The self-tanning composition of claim 4, further comprising of, by weight: about 10% glycerin; about 3% dipropylene glycol; about 0.45% preservative; about 3% PEG-2 Dimeadowfoam-Amidoethylmonium Methosulfate; about 0.5% Polyquaternium-37; about 10% of a mixture of Mineral Oil (and) Ethylene/Propylene/Styrene Copolymer (and) Butylene/Ethylene/Styrene Copolymer; about 2% Isopropyl Palmitate; about 5% shea butter; about 2% of a mixture of Dimethicone and Dimethiconol; about 3.5% dihydroxyacetone; about 0.5% Erythrulose; deioinized water to 100%, about 0.5% fragrance.

9. The self-tanning composition of claim 1, wherein the ratio of said PEG-2-dimeadowfoam-amidoethylmonium-methosulfate to dihydroxyacetone is from about 1:5 to about 5:1.

10. A self-tanning composition for application to wet skin consisting of, by weight: about 10% glycerin; about 7% dipropylene glycol; about 3% PEG-2 Dimeadowfoam-Amidoethylmonium Methosulfate; about 0.75% Polyquaternium-37; about 0.75% Ceteareth-20; about 2.5% of a mixture of Mineral Oil (and) Ethylene/Propylene/Styrene Copolymer (and) Butylene/Ethylene/Styrene Copolymer; about 2% Isopropyl Palmitate; about 4.5% Ethylhexyl Isononanoate; about 3.5% of a mixture of Dimethicone and Dimethiconol; about 3.5% Dihydroxyacetone; about 0.1% Erythrulose; deioinized water, fragrance and preservative to 100%.

11. A self-tanning composition for application to wet skin consisting of, by weight: about 20% glycerin; about 5% dipropylene glycol; about 0.5% PEG-2 Dimeadowfoam-Amidoethylmonium Methosulfate; about 0.75% Polyquaternium-37; about 0.25% Ceteareth-20; about 7.5% of a mixture of Mineral Oil (and) Ethylene/Propylene/Styrene Copolymer (and) Butylene/Ethylene/Styrene Copolymer; about 2% Isopropyl Palmitate; about 4.5% Ethylhexyl Isononanoate; about 1.75% of a mixture of Dimethicone and Dimethiconol; about 1.7% Dihydroxyacetone; about 0.1% Erythrulose; deioinized water, fragrance and preservative to 100%.

* * * * *